US007682627B2

(12) United States Patent
Nelson et al.

(10) Patent No.: US 7,682,627 B2
(45) Date of Patent: *Mar. 23, 2010

(54) ARTIFICIAL LOW-DENSITY LIPOPROTEIN CARRIERS FOR TRANSPORT OF SUBSTANCES ACROSS THE BLOOD-BRAIN BARRIER

(75) Inventors: Thomas Nelson, Rockville, MD (US); Alessandro Quattrone, Prato (IT); Daniel Alkon, Bethesda, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/648,808

(22) Filed: Jan. 3, 2007

(65) Prior Publication Data
US 2007/0134313 A1 Jun. 14, 2007

Related U.S. Application Data

(63) Continuation of application No. 10/724,833, filed on Dec. 2, 2003, now Pat. No. 7,220,833.

(60) Provisional application No. 60/430,476, filed on Dec. 3, 2002.

(51) Int. Cl.
  A61K 38/00  (2006.01)
  A61K 31/58  (2006.01)
  A61K 39/395 (2006.01)
  A61K 39/00  (2006.01)
  A61K 9/127  (2006.01)
  A61K 9/50   (2006.01)

(52) U.S. Cl. .................. 424/450; 424/490; 424/133.1; 530/350; 514/12; 514/2; 514/34; 977/906

(58) Field of Classification Search ........................ None
See application file for complete search history.

(56) References Cited

U.S. PATENT DOCUMENTS

| 3,828,106 | A | * | 8/1974 | Rudel ......................... 514/170 |
| 5,324,821 | A | | 6/1994 | Favre et al. |
| 5,985,941 | A | * | 11/1999 | Counsell et al. .............. 516/56 |
| 6,245,753 | B1 | | 6/2001 | Byun et al. |
| 6,288,040 | B1 | | 9/2001 | Muller et al. |

FOREIGN PATENT DOCUMENTS

| EP | 0 277 849 A1 | 8/1988 |
| WO | WO 87/02061 | 4/1987 |
| WO | WO 92/21330 | 12/1992 |
| WO | WO 98/13385 | 4/1998 |
| WO | WO 99/04761 | 2/1999 |
| WO | WO 00/64484 | * 11/2000 |

OTHER PUBLICATIONS

Wu, Dafang et al., Pharmacokinetics and Brain Uptake of Biotinylated Basic Fibroblast Growth Factor Conjugated to a Blood-Brain Barrier Drug Delivery System, Journal of Drug Targeting, 2002 vol. 10(3), pp. 239-245.
Mims, Marth P. et al., "Effect of Particle Size and Temperature on the Conformation and Physiological Behavior of Apolipoprotein E Bound to Model Lipoprotein Particles," Biochemistry 1990, 29, 6639-6647.
Hotlzman, David M., "Role of apoE/AB Interactions in the Pathogenesis of Alzheimer's Disease and Cerebral Amyloid Angiopathy," Journal of Molecular Neuroscience, vol. 17, 2001. pp. 147-155.
Xu. J et al., "Tissue-specific regulation by vitamin D3 of a novel protein containing ankyrin-like repeats," Molecular and Cellular Endocrinology, Jan. 3, 1997, vol. 126, No. 1, pp. 101-107 XP0009027368.
International Search Report for PCT/IB03/05558 dated Aug. 11, 2004.
Nakla, T. et al., Liposomel Formulations—Article: "Issues Associated with Large-Scale Production of Liposomal Formulations", Drug Delivery Back Issues, pp. 1-6.
Westesen, K. et al., "Characterization of Native and Drug-Loaded Human Low Density Lipoprotiens", Journal of Pharmaceutical Sciences, vol. 84, No. 2, Feb. 1995, pp. 139-147.
Versluis, A.J. et al., "Stable Incorporation of a Lipophilic Daunorubicin Prodrug into Apolipoprotein E-Exposing Liposomes Induces Uptake of Prodrug via Low-Density Lipoprotein Receptor in Vivo", The Journal of Pharmacology and Experimental Therapeutics, vol. 289, No. 1, pp. 1-7.
Ginsburg, G.S. et al. "Microemulsions of Phospholipids and Cholesterol Esters—Protein-Free Models of Low Density Lipoprotein", The Journal of Biological Chemistry, vol. 257, No. 14, Issue of Jul. 25, pp. 8216-8227, 1982.
Rensen, P. C. N. et al. "Particle size determines the specificity of apolipoprotein E-containing triglyceride-rich emulsions for the LDL receptor versus hepatic remnant receptor in Vivo", Journal Lipid Research, vol. 38, 1997, pp. 1070-1084.
Webster's Collegiate Dictionary—Tenth Edition- p. 66, 1996.
Rensen et al., "Human Recombinant Apolipoprotein E-Enriched Liposomes Can Mimic Low-Density Lipoproteins as Carriers for the Site-Specific Delivery of Antitumor Agents." Molecular Pharmacology, 52:445-455, Sep. 1997, XP-002273272.
Kreuter et al., "Apolipoprotein-mediated Transport of Nanoparticle-bound Drugs Across the Blood-Brain Barrier." Journal of Drug Targeting, 2002 vol. 10(4) pp. 317-325, XP009027368.
Versluis et al., "Synthesis of a Lipophilic Daunorubicin Derivative and Its Incorporation into Lipidic Carriers Developed for LDL Receptor-Mediated Tumor Theraphy." Pharmaceutical Researh, vol. 15, No. 4, 1998, XP009036781.

(Continued)

Primary Examiner—Lisa J Hobbs
(74) Attorney, Agent, or Firm—Milbank, Tweed, Hadley & McCloy, LLP

(57) ABSTRACT

This invention relates to a highly efficient artificial low-density lipoprotein (LDL) carrier system for the targeted delivery therapeutic agents across the blood-brain barrier (BBB). In particular, this invention relates to artificial LDL particles comprised of three lipid elements: phosphatidyl choline, fatty-acyl-cholesterol esters, and at least one apolipoprotein. The present invention further relates to compositions, methods and kits comprising artificial LDL particles for targeting drugs to and across the BBB for the prevention and treatment of brain diseases.

36 Claims, 6 Drawing Sheets

OTHER PUBLICATIONS

Masquelier et al., "Low Density Liproprotein as a Carrier of Cytostatics in Cancer Chemotherapy: Study of Stability of Drug-Carrier Complexes in Blood." Journal of Drug Trageting, 2000, vol. 8, No. 3, pp. 155-164, XP009027575.

Masquelier et al., "Plasma stability and cytotoxicity of lipophilic daunorubicin derivatives incorporated into low density lipoproteins." Eur. J. Med. Chem. 35 (2000) 429-438.

Murtha et al., "Synthesis of the Cholesteryl Ester Prodrugs Cholesteryl Ibuprofen and Cholesteryl Flufenamate and Their Formulation into Phospholipid Microemulsions." 1088 Journal of Pharmaceutical Sciences, 83 Sep. 1994, No. 9, DC, US, XP 00465804, pp. 1222-1228.

Rensen et al., "Recombinant lipoproteins: lipoprotein-like lipid particles for drug targeting." Advanced Drug Delivery Reviews 47 (2001) 251-276, XP-002273271.

Bhattacharya et al., "Novel distamycin analogues: facile synthesis of cholesterol conjugates of distamycin-like oligopeptides." Tetrahedron Letters 42 (2001) 3499-3502, XP-002299552.

Reinhardt, R.R. et al., "Insulin-Like Growth Factors Cross the Blood-Brain Barrier," Endocrinology, vol. 135, No. 5, (1994) pp. 1753-1761.

Witt, Ken A. et al., "Insulin Enhancement of Opioid Peptide Transport across the Blood-Brain Barrier and Assessment of Analgesic Effect," The Journal of Pharmacology and Experimental Therapeutics, vol. 295, No. 3, 3100/866639, (2000) pp. 972-978.

Rigotti, Attilio et al., "The Class B Scavenger Receptors SR-BI and CD36 Are Receptors for Anionic Phospholipids," The Journal of Biological Chemistry, vol. 270, No. 27, Issue of Jul. 7, pp. 16221-16224, 1995.

Bradley, William et al., "Low-density Lipoprotein Receptor Binding Determinants Switch from Apolipoprotein E to Apolipoprotein B during Conversion of Hypertriglyceridemic Very-low-density Lipoprotein to Low-density Lipoproteins," The Journal of Biological Chemistry, vol. 259, No. 23, Issue of Dec. 10, pp. 14728-14735, 1984.

Veingergs, Isaac et al., "Neurotoxic Effects of Apolipoprotein E4 are Mediated via Dysregulation of Calcium Homeostasis," Journal of Neuroscience Research 67:379-387 (2002).

Shibata, Masayoshi et al., "Clearance of Alzheimer's amyloid-B1-40 peptide from brain by LDL receptor-related protein-1 at the blood-brain barrier," The Journal of Clinical Investigation, Dec. 2000, vol. 106, No. 12, pp. 1489-1499.

Alyaudtin, Renad et al. "Interaction of Poly(butylcyanoacrylate) Nanoparticles with Blood-Brain Barrier in vivo and in vitro," Journal of Drug Targeting, 2001, vol. 9, No. 3, pp. 209-221.

Kang, Young-Sook et al., "Stability of the Disulfide Bond in an Avidin-Biotin Linked Chimeric Peptide During in vivo Transcytosis Through Brain Endothelial Cells," Journal of Drug Targeting, 2000, vol. 8, No. 6, pp. 425-434.

Pardridge, William M., "CNS Drug Design Based on Principles of Blood-Brain Barrier Transport," J. Neurochem., vol. 70, No. 5, 1998, pp. 1781-1792.

Bickel, Ulrich et al., "Delivery of peptides and proteins through the blood-brain barrier," Advanced Drug Delivery Reviews, 10 (1993) 205-245.

Hevonoja, Tiia et al., "Structure of low density lipoprotein (LDL) particles: Basis for understanding molecular changes in modified LDL," Biochemica et Biophysica Acta 1488 (2000) 189-210.

Pardrige, William M. et al., "Blood-Brain Barrier: Interface Between Internal Medicine and the Brain," Annals of Internal Medicine, 1986; 105: 82-95.

Wu, Dafang et al., Pharmacokinetics and Brain Uptake of Biotinylated Basic Fibroblast Growth Factor Conjugated to a Blood-Brain Barrier Drug Delivery System, Journal of Drug Targeting, 2002 vol. 10(3), pp. 239-245.

Mims, Marth P. et al., "Effect of Particle Size and Temperature on the Conformation and Physiological Behavior of Apolipoprotein E Bound to Model Lipoprotein Particles," Biochemistry 1990. 29, 6639-6647.

Hotlzman, David M., "Role of apoE/AB Interactions in the Pathogenesis of Alzheimer's Disease and Cerebral Amyloid Angiopathy," Journal of Molecular Neuroscience, vol. 17, 2001. pp. 147-155.

Xu. J et al., "Tissue-specific regulation by vitamin D3 of a novel protein containing ankyrin-like repeats," Molecular and Cellular Endocrinology, Jan. 3, 1997, vol. 126, No. 1, pp. 101-107 XP0009027368.

International Search Report for PCT/IB03/05558 dated Aug. 11, 2004.

Westesen, K. et al., "Characterization of Native and Drug-Loaded Human Low Density Lipoprotiens", Journal of Pharmaceutical Sciences, vol. 84, No. 2, Feb. 1995, pp. 139-147.

Versluis, A.J. et al., "Stable Incorporation of a Lipophilic Daunorubicin Prodrug into Apolipoprotein E-Exposing Liposomes Induces Uptake of Prodrug via Low-Density, Lipoprotein Receptor in Vivo", The Journal of Pharmacology and Experimental Therapeutics, vol. 289, No. 1, pp. 1-7, (1999).

Naklha et al. (2002) Drug Delivery Technology 2(4): 1-6.

* cited by examiner

ARTIFICIAL LOW-DENSITY LIPOPROTEIN CARRIERS FOR TRANSPORT OF SUBSTANCES ACROSS THE BLOOD-BRAIN BARRIER

This application is a continuation of U.S. application Ser. No. 10/724,833 filed on Dec. 2, 2003, now U.S. Pat. No. 7,220,833, which claims priority to U.S. Provisional Application Ser. No. 60/430,476 that was filed on Dec. 3, 2002.

TECHNICAL FIELD OF THE INVENTION

This invention relates to the use of artificial low-density lipoprotein (LDL) particles of efficiently target and deliver substances across the blood-brain barrier (BBB). The invention further provides artificial LDL particle compositions, methods, and kits for the prevention and treatment of a variety of brain diseases.

BACKGROUND OF THE INVENTION

The blood-brain barrier (BBB), while providing effective protection to the brain against circulating toxins, also creates major difficulties in the pharmacological treatment of brain diseases such as Alzheimer's disease, Parkinson's disease, and brain cancer. Most charged molecules, and most molecules over 700 Daltons in size, are unable to pass through the barrier, and smaller molecules may be conjugated in the liver. These factors create major difficulties in the pharmacological treatment of diseases of the brain and central nervous system (CNS), such as Alzheimer's disease, Parkinson's disease, bacterial and viral infections and cancer.

Many therapeutic agents for the treatment of diseases and disorders of the brain and CNS are sufficiently hydrophilic to preclude direct transport across the BBB. Furthermore, these drugs and agents are susceptible to degradation in the blood and peripheral tissues that increase the dose necessary to achieve a therapeutically effective serum concentration. The present invention provides a method of delivering therapeutic agents to the BBB by encapsulating the therapeutic agent in an artificial low-density lipoprotein particle (LDL). The LDL of this invention facilitates transport of therapeutic agents across the BBB by transcytosis. Since most drugs and therapeutic agents that are too hydrophilic to cross the BBB are also too hydrophilic to be incorporated into an LDL particle, the present invention provides a method for producing conjugates of the therapeutic agents with an LDL component that facilitates its incorporation into an LDL particles, transport across the BBB and subsequent release of the therapeutic agent into the cell.

Prior methods for delivery drugs across the BBB involve three general categories: (1) liposome-based methods, where the therapeutic agent is encapsulated within the carrier; (2) synthetic polymer-based methods, where particles are created using synthetic polymers to achieve precisely-defined size characteristics; and (3) direct conjugation of a carrier to a drug, where the therapeutic agent is covalently bound to a carrier such as insulin.

A. Liposomes

Liposomes are small particles that form spontaneously when phospholipids are sonicated in aqueous solution, and consist of a symmetrical lipid bilayer configured as a hollow sphere surrounding an aqueous environment. This has appeal as a means of transporting water-soluble drugs through the cell membrane, as the phospholipid can be absorbed in the plasma membrane, which automatically releases the contents of the liposomes into the cytosol. More successful variations of this technique include the use of cationic lipids, which can cooperatively create nanopores in the membrane. Cationic lipids are extensively used in cell culture to introduce water-soluble materials such as DNA molecules into cultured cells for experimentation.

Liposomes are attractive for transporting drugs across the BBB because of their large carrying capacity. However, liposomes are generally too large to effectively cross the BBB, are inherently unstable, and their constituent lipids are gradually lost by absorption by lipid-binding proteins in the plasma. For example, in some studies, the large size of the liposomes used produced microembolisms that gave a false impression of brain uptake. In some studies, liposomes were co-injected with Polysorbate 80, a detergent that can disrupt the BBB, as a stabilizing agent. The disruption of the BBB by the Polysorbate 80 in these studies may be responsible for any observed transport across the BBB.

Consequently, liposomes have had a checkered history as vehicles for transporting drugs across the BBB. Several attempts have been made to direct the liposome to particular cellular targets. Peptidomimetic mAbs that target endogenous receptors of the BBB have been used to target pegylated immunoliposomes to various BBB receptors, with the aim of achieving receptor-mediated uptake. However, this approach also requires the expensive production, testing and governmental approval of monoclonal antibodies. Because mAbs are typically produced in mice, and are susceptible to degradation, introduction of a peptidomimetic mAb would not only face significant regulatory obstacles but would prove difficult to deploy in a patient environment.

Immunoliposomes, for example, have been constructed in a process that involves covalent attachment of monoclonal antibodies (mAbs) to the surface of the liposome. Since these immunoliposomes are immediately coated with plasma proteins that trigger uptake by the reticuloendothelial systems (RES), a system that avidly destroys mAb-conjugated liposomes, immunoliposomes have been treated with polyethylene glycol (PEG) in a process known as pegylation. Unfortunately, the PEG molecules interfere with the mAb, rendering them non-specific due to steric interference. Huwyler et al. (1996) *Proc. Nat'l. Acad. Sci USA* 93: 14164-14169 avoided this problem by creating immunoliposomes with a maleimide moiety at the tip of the PEG tail, which could be conjugated with a thiolated mAb. These pegylated OX26 immunoliposomes, which were prepared with daunomycin in their interiors, were shown to be more stable in plasma than the free therapeutic agent or plain, unpegylated liposomes. Confocal microscopy, however, has shown that although the liposomes were endocytosed into rat brain capillaries, they did not reach brain cells and remained attached to endothelial cells. Thus, pegylated and maleimide-treated liposomes appear to be relatively ineffective as drug delivery vehicles.

In 1997, Dehouck et al. discovered that the LDL receptors, which binds ApoE, is involved in transcytosis of LDL across the BBB. In a series of three publications, Versluis et al. described the use of ApoE-enriched liposomes to deliver daunorubicin to cancer cells in mice. ApoE was selected as an LDL-receptor targeting protein based on the finding that tumor cells express high levels of LDL receptors on their membranes. Versluis et al. (1998) also proposed using natural LDL, but this experiment was not attempted and subsequent papers focused exclusively on ApoE-enriched liposomes. Versluis et al. (1999) examined the tissue distribution of daunorubicin, but there are no data related to brain uptake, indicating that this method was not envisaged as a means for transporting daunorubicin across the BBB.

Additionally, the conjugation chemistry used by Versluis et al. is different from that used in the present Invention. To anchor the drug to the liposome membrane, the authors coupled 3α-O-(oleoyl)-4β-cholanic acid (an ester of lithocholic acid) to the tetrapeptide Ala-Leu-Ala-Leu, which was in turn covalently linked to the hydrophilic anti-tumor agent daunorubicin. Thus, tumors were treated with conjugated, not free, daunorubicin. Although lithocholic acid is a steroid that already contains an activatable acid group, the acid group is located on the steroid side chain instead of the 3-OH position, which results in a reaction product with less desirable features. Free daunorubicin can be produced only after cleavage by proteases fund in the highly acidic lysosome, which would expose the conjugated during or agent to degradation by proteases, acid and other hydrolytic enzymes. The therapeutic agent would then be released into the intralysosomal space where it could undergo further degradation and expulsion from the cell.

In contrast, the conjugates of the present invention preferably provides for attachment of the therapeutic agent via an ester linkage that can be easily cleaved in the cytosol and consequently escape the harsh lysosomal conditions needed by the method of Versluis et al. Thus, a therapeutic agent conjugated by the present method would be more likely to survive the journey to its target and to be released at the target in an efficient manner. It is also more likely to be transported across the BBB than a liposome.

The method of Versluis et al. also requires a large number of solid-phase peptide chemistry steps to synthesize the tetrapeptide, and several additional steps to conjugate it with FMOC and react the conjugate with lithocholic acid and finally with the drug. The present invention uses a much smaller number of steps, each of which produces nearly quantitative yield. Thus the present invention also offers improved efficiency and lower cost.

Other liposomal formulations of doxyrubicin are currently in clinical use as possible treatments for cancer; however, no products have been introduced that use LDL.

Demeule et al. found that the protein melanotransferrin (p97) is transported by transcytosis across the BBB and concluded that an LDL receptor was involved, suggesting that this protein be employed as a drug delivery system.

B. Synthetic Polymers

Synthetic polymers such as poly(butyl cyanoacrylate) or polyacrylamide covered with Polysorbate 80 have also been tried. These polymers are appealing because the particles are sufficiently hydrophilic to be water-soluble, yet are able to maintain their structural form for long periods, which protects the therapeutic agent from uptake into the liver and kidney where it is subject to natural detoxification process. In both cases, uptake is generally supposed to occur by passive diffusion across the cell membrane or as a defensive uptake by clathrin-coated vesicles. In the former case, the therapeutic agent is then trapped in an endothelial cell, where it is not much closer to the target than before, whereas in the latter case, the therapeutic agent is transported to a lysosome, which is a highly acidic compartment in the cell containing proteases and other digestive enzymes analogous to stomach contents. Thus, in the latter case, the therapeutic agent must remain stable throughout more extreme conditions. In neither case is the drug carried across the cell and ejected into the brain parenchyma, which is the desired result. Thus, it is not surprising that neither of these two methods has achieved much clinical use.

Numerous researchers have tried various modifications of the approaches described above to improve carrier uptake across the BBB with limited success. For example, Kreuter et al. (2002) *J. Drug Target* 10(4): 317-25 engineered synthetic particles that contained various apolipoproteins that would bind to the apolipoprotein receptors located at the BBB. They demonstrated transport of drugs bound to poly(butyl cyanoacrylate) nanoparticles and coated them with Polysorbate 80. Uptake required coating with Polysorbate 80, ApoE or ApoB. Apolipoproteins A11, C11, or J coatings did not work. However, because these nanoparticles are not naturally occurring, they may have undesirable side effects. Acrylate polymers are particularly notorious for initiating autoimmune responses; the chemically-related polymer poly(acrylamide) is often used as an adjuvant.

Alyaudin et al. (2001) *J. Drug Target* 9(3): 209-21 used poly(butylcyanoacrylate) nanoparticles overcoated with Polysorbate 80 to transport [3H]-dalargin across the BBB and surmised the process was one of endocytosis followed by possible transcytosis. This polymer may have immunological complications as well.

C. Therapeutic Agent Conjugates

Direct conjugation of pharmacological agents with the substances that can be transported across the BBB, such as insulin, has also been attempted. Insulin and insulin-like growth factors are known to cross the blood brain barrier by specialized facilitated diffusion systems. (Reinhardt et al. (1994) *Endocrinology* 135(5): 1753-1761). Insulin is taken up by transcytosis mediated by the endothelial insulin receptor (Pardridge et al. (1986) *Ann. Intern. Med.* 105(1): 82-95). Specific transporters also exist for glucose and for large amino acids such as tryptophan. However, the specificity of the insulin transporter has proved to be too high to allow pharmacological agents covalently linked to insulin to cross into the brain. Similar results have been obtained with glucose and amino acid conjugates, whose uptake has been observed to obey the same general principles as other low-molecular weight substances, with only uncharged molecules below 700 Da achieving significant access to the brain. The inconvenience in devising chemical syntheses of conjugated forms of biomolecules, the risk of creating unanticipated toxic effects, and the likely necessity of obtaining FDA approval for an entirely novel compound has dampened enthusiasm for this approach.

Transport vectors, which are proteins such as cationized albumin, or the OX26 monoclonal antibody to the transferrin receptor undergo absorptive-mediated and receptor-mediated transcytosis through the BBB, respectively. These have been used to transport small amounts of drug. This process, suffers from the high expense and difficulty of producing monoclonal antibodies and cationized albumin and is not applicable to other types of molecules. Also, cationized proteins have been shown to be toxic due to their immunogenicity and the formation of immune complexes that are deposited in the kidney.

Wu et al. (2002) *J. Drug Target* 10(3): 239-45 showed transport of human basic fibroblast growth factor (bFGF), a protein neuroprotective agent, across the BBB using a drug delivery vector consisting of a conjugate of streptavidin (SA) and the murine OX26 monoclonal antibody against the rat transferrin receptor, and the conjugate of biotinylated bFGF (bio-bFGF) bound to a vector designated bio-bFGF/OX26-SA. Although they showed avid uptake of [$^{125}$I] labeled bio-bFGF into peripheral organs, only 0.01% of the injected dose was taken up per gram brain. Also, this procedure requires covalent modification of the drug, and may be useful only for limited classes of drugs. The carrier also contains mouse monoclonal antibodies as a component, which would cause an immune response in the patient.

Kang et al. (2000) *J. Drug Target* 8(6): 425-34 also used an avidin-biotin linked chimeric peptide to transport a peptide across the BBB but achieved only 0.12% of the injected dose taken up per gram of tissue. Kang and Pardridge (*Pharm. Res.* 11: 1257-1264) conjugated cationized human serum albumin with neutral light avidin, and then bound it to radiolabeled biotin. The biotin/cHSA/NLA complex was stable in blood for up to 24 h, but the conjugate was selectively degraded in brain to release free biotin. As mentioned above, cationized proteins have been shown to be toxic due to their immunogenicity.

Cationized monoclonal antibodies (mAbs) have also been used. Pardridge (*J. Neurochem.* 70: 1781-2) showed by confocal microscopy that the native humanized 4D5 MAb crossed the BBB by absorptive-mediated transcytosis, but only after cationization of the protein. This process, however, suffers from the high expense of producing and chemically modifying monoclonal antibodies and is not applicable to other types of molecules.

Witt et al. (2000) *J. Pharmacol. Exp. Ther.* 295(3): 972-8 used insulin to transport delta-opioid receptor-selective peptide D-penicillamine (DPDPE), a Met-enkephalin analog, across the BBB. Insulin, however, presents numerous hazards that limit its use as a therapeutic strategy. Also, other researchers have found the insulin receptor to be extremely selective. Thus, in addition to the difficulty in producing chimeric peptides, this strategy is limited to a narrow class of pharmaceutical agents.

Other researchers have attempted to conjugate drugs to glucose, for instance using glycopeptides. However, no significant transport of any glycopeptide via the BBB Glut1 transporter has ever been demonstrated. Attempts to use the high-transport rate of carrier-mediated transporters such as the Glut1 glucose transporter, the choline transporter, or the LAT1 large amino acid transporter have foundered on the problem that carrier transporters are too selective to accept conjugated substrates. They also suffer from the problem that p-glycoprotein, a member of the multidrug resistance gene, rapidly acts to actively remove many small molecules, including any drugs that manage to get across the barrier, from the brain.

In addition to the LDL receptor, the BBB also contains type II scavenger receptors (SR), which bind LDL with high affinity. The scavenger receptor is particularly good with modified forms of LDL such as acetylated LDL. Binding to the SR results only in endocytosis and not the desired transcytosis. Rigotti et al. (1995) *J. Biol. Chem.* 270: 16221-4 found that acetylated LDL is not transported across the BBB, whereas cationized bovine IgG was more effective Bickel et al. (1993) *Adv. Drug. Del. Rev.* 10: 205-245. The failure to demonstrate transcytosis with acetylated LDL discouraged many researchers from attempting further experiments with LDL.

Protter et al. (WO 87/02061) describe a drug delivery system that uses peptides derived from apolipoproteins, such as ApoE and ApoB, which are covalently attached to the pharmaceutical agent, or to a carrier containing the agent. However, the use of molecular conjugates would only be limited to a small number of drug classes, and subject to many of the same problems discussed above.

Müller et al. (U.S. Pat. No. 6,288,040) describe the use of synthetic poly(butyl cyanoacrylate) particles to which ApoE molecules are covalently bound. The surface of the particles are further modified by surfactants or covalent attachment of hydrophilic polymers. As stated above, because these particles are not naturally occurring, they may have a variety of undesirable side effects.

Samain et al. (WO 92/21330) describe the use of synthetic particulate carriers containing lipids that are covalently attached to a solid, hydrophilic core and that also contain ApoB for delivery of substances to tumors or macrophages. However, they do not disclose any utility of such vectors for delivering drugs across the BBB.

SUMMARY OF THE INVENTION

This invention relates to the use of artificial low-density lipoprotein (LDL) particles to target and deliver substances across the blood brain barrier into the brain. Yet another object of the invention is the synthesis of LDL carriers that are structurally stable, non-immunogenic, and protect a broad variety of drugs from degradation, inactivation, hydrolysis, conjugation, and uptake into non-target tissues. The present invention provides LDL particles to be used as carriers of therapeutic agents and improved methods of delivering such drugs and agents across the BBB as compared to previously described methods. Unlike liposomes, for example, LDL particles are solid particles that consequently have greater structural stability than liposomes. A further object of the present invention is to provide compositions, methods, and kits comprising LDL carriers for the treatment and prevention of a broad variety of brain diseases.

The present invention provides a process for conjugating hydrophilic therapeutic agents with cholesterol to facilitate incorporation of the conjugated therapeutic agent into an artificial LDL particle of the present invention. In a preferred embodiment, the present invention provides cholesterol-conjugated adriamycin and tetracycline. The processes and resultant cholesterol conjugates and compositions of such conjugates are useful in providing an LDL particle for the purpose of transporting therapeutic agents across the brain barrier by transcytosis, which is a receptor-mediated process that operates in brain capillary endothelial cells as a means of importing cholesterol and essential fatty acids into the brain, that will facilitate and improve treatment of a variety of diseases and disorders of the brain and CNS. Alternatively, the cholesterol conjugates of the present invention are useful for the delivery of the corresponding therapeutic agent across the BBB without incorporation of the conjugate into the LDL particles of the present invention.

In a preferred embodiment, the cholesterol conjugates of the present invention are linked through an ester linkage that allows release of the therapeutic agent from the conjugate by the action of ubiquitous endogenous esterases. Inclusion of the cholesterol conjugates of the present invention into an LDL particle of the present invention protects the cholesterol conjugates from hydrolysis by these esterases.

The present invention further provides artificial LDL particles comprising egg yolk phosphatidyl choline (EYPC), cholesterol oleate, and apolipoprotein E3 (ApoE3). The components lipids form solid particles that contain three layers: a solid lipid core consisting of cholesterol, cholesterol esters, and an active agent; a middle interfacial layer, consisting of a mixture of fatty acid chains of phosphatidyl choline; and a surface layer, consisting of phospholipid head groups and ApoE3.

The LDL particles of the invention significantly increase the targeting of active agents to capillary endothelial cells and facilitate transport across the blood brain junction by transcytosis. The protein and phospholipid components that surround the therapeutic agent also act to protect it from degradation and uptake into non-target cells.

The present invention also relates to methods of treating diseases, ailments and conditions based upon the artificial LDL particle-facilitated transfer of agents. For example, the present invention provides pharmaceutical compositions and methods for treating various brain diseases comprising targeting specific agents to brain tissues using the artificial LDL particles of the invention.

The present invention provides an artificial LDL particle comprising an outer phospholipid monolayer and a solid lipid core, wherein the outer phospholipid monolayer comprises at least one apolipoprotein and the solid lipid core contains at least one therapeutic agent. In one embodiment, the at least one apolipoprotein is selected from the group consisting of ApoA, ApoB, ApoC, ApoD, or ApoE, or an isoform of one of the apolipoproteins, or a combination of lipoproteins and/or isoforms. In a preferred embodiment, the at least one apolipoprotein is ApoE. In a more preferred embodiment, the at least one apolipoprotein is selected from the group consisting of ApoE2, ApoE3 and ApoE4. The present invention also relates to artificial LDL particles further comprising additional targeting molecules or agents that enhance the targeted delivery of the LDL complexes to brain tissue. In the most preferred embodiment, the at least one apolipoprotein is ApoE3, either alone or in combination with one or more oxysterols and/or an additional apolipoprotein selected from the group consisting of ApoB and ApoE4.

The present invention provides an artificial LDL particle for the transport of therapeutic agents across the blood-brain barrier. In a preferred embodiment, the at least one therapeutic agent is selected from the group consisting of: amino acids, peptides, proteins, carbohydrates and lipids. In another embodiment, the at least one therapeutic agent is a conjugate formed between cholesterol and an agent selected from the group consisting of: amino acids, peptides, proteins, carbohydrates and lipids. In preferred embodiments, the at least one therapeutic agent is selected from the group consisting of: neurotrophic factors, growth factors, enzymes, neurotransmitters, neuromodulators, antibiotics, antiviral agents, antifungal agents and chemotherapeutic agents.

The outer phospholipid monolayer of the artificial LDL particle may comprise any phospholipid or combination of phospholipids, including but not limited to phosphatidic acid, phosphatidylcholine, phosphatidylethanolamine, phosphatidylserine, phosphatidylglycerol, and the like. In a preferred embodiment, the outer phospholipid monolayer comprises phosphatidylcholine and at least one apolipoprotein.

The artificial LDL particles of the present invention are particles with a preferred diameter between about 15 and 50 nm. In a more preferred embodiment, the artificial LDL particles have a diameter between about 20 and 30 nm. The artificial LDL particles of the present invention have a preferred density between about 1.00 and 1.07 g/ml. In a more preferred embodiment, the artificial LDL particles have a density between about 1.02 and 1.06 g/ml. Furthermore, the artificial LDL particles of the present invention have a serum stability of at least two hours.

The present invention provides artificial LDL particles that are transported across the BBB by transcytosis. In a preferred embodiment, the particles of the present invention have at least a 3-fold greater uptake specificity for brain compared to liver.

The solid lipid core of the artificial LDL particles of the present invention may comprise one or more lipids, including but not limited to triacylglycerols, cholesterol, cholesterol esters, fatty-acyl esters, and the like. In a preferred embodiment, the solid lipid core comprises cholesterol esters wherein the cholesterol is esterified with a saturated fatty acid, including but not limited to myristate, palmitate, stearate, arachidate, lignocerate, and the like, or an unsaturated fatty acid, including but not limited to palmitoleate, oleate, vaccenate, linoleate, linolenate, arachidonate, and the like. In a more preferred embodiment, the solid lipid core comprises the cholesterol ester cholesterol oleate. In a preferred embodiment, the solid lipid core of the artificial LDL particles of the present invention comprise at least one therapeutic agent that is a conjugate formed between cholesterol and adriamycin or tetracycline. In a preferred embodiment, the cholesterol and therapeutic agent of the conjugate are linked by an ester bond.

The present invention also provides compositions for delivery of a therapeutic agent across the blood-brain barrier comprising an artificial LDL particle of the present invention and a pharmaceutically acceptable carrier.

The present invention also provides a conjugate comprising cholesterol linked to a therapeutic agent selected from the group consisting of: amino acids, peptides, proteins, carbohydrates and lipids. In a preferred embodiment, the therapeutic agent is selected from the group consisting of: neurotrophic factors, growth factors, enzymes, neurotransmitters, neuromodulators, antibiotics, antiviral agents, antifungal agents and chemotherapeutic agents. In a more preferred embodiment, the therapeutic agent of the conjugates of the present invention are adriamycin or tetracycline. In the most preferred embodiment, the cholesterol and therapeutic agents of the conjugates of the present invention are linked by an ester bond. Each of the conjugates of the present invention may be combined with a pharmaceutically acceptable carrier, as described herein, and used in any of the methods of drug delivery of the present invention.

The present invention also provides a method of producing an artificial LDL particle of the present invention comprising the steps of: 1) suspending phospholipids containing conjugated or unconjugated therapeutic agent in a buffer solution; 2) sonicating the solution to form the outer phospholipid monolayer and solid lipid core; and 3) adding a solution comprising at least one apolipoprotein, wherein the apolipoprotein is incorporated into the outer phospholipid monolayer. In a preferred embodiment, the artificial LDL particles produced by the methods of the present invention have a diameter between 10 and 50 nm.

The present invention also provides a method for delivery a substance across the blood-brain barrier, said method comprising administering an effective amount of any of the compositions of the present invention to a mammal in need thereof.

The present invention also provides kits for delivering substances across the blood-brain barrier, wherein said kits comprise a container containing the any of the compositions of the present invention and instructions for use.

The present invention also provides for the use of the conjugates, artificial LDL particles and compositions of the present invention in the production of a medicament for the treatment of diseases of the brain and central nervous system (CNS), such as Alzheimer's disease, Parkinson's disease, bacterial and viral infections and cancer.

DETAILED DESCRIPTION OF THE INVENTION

Definitions

Figure 1:
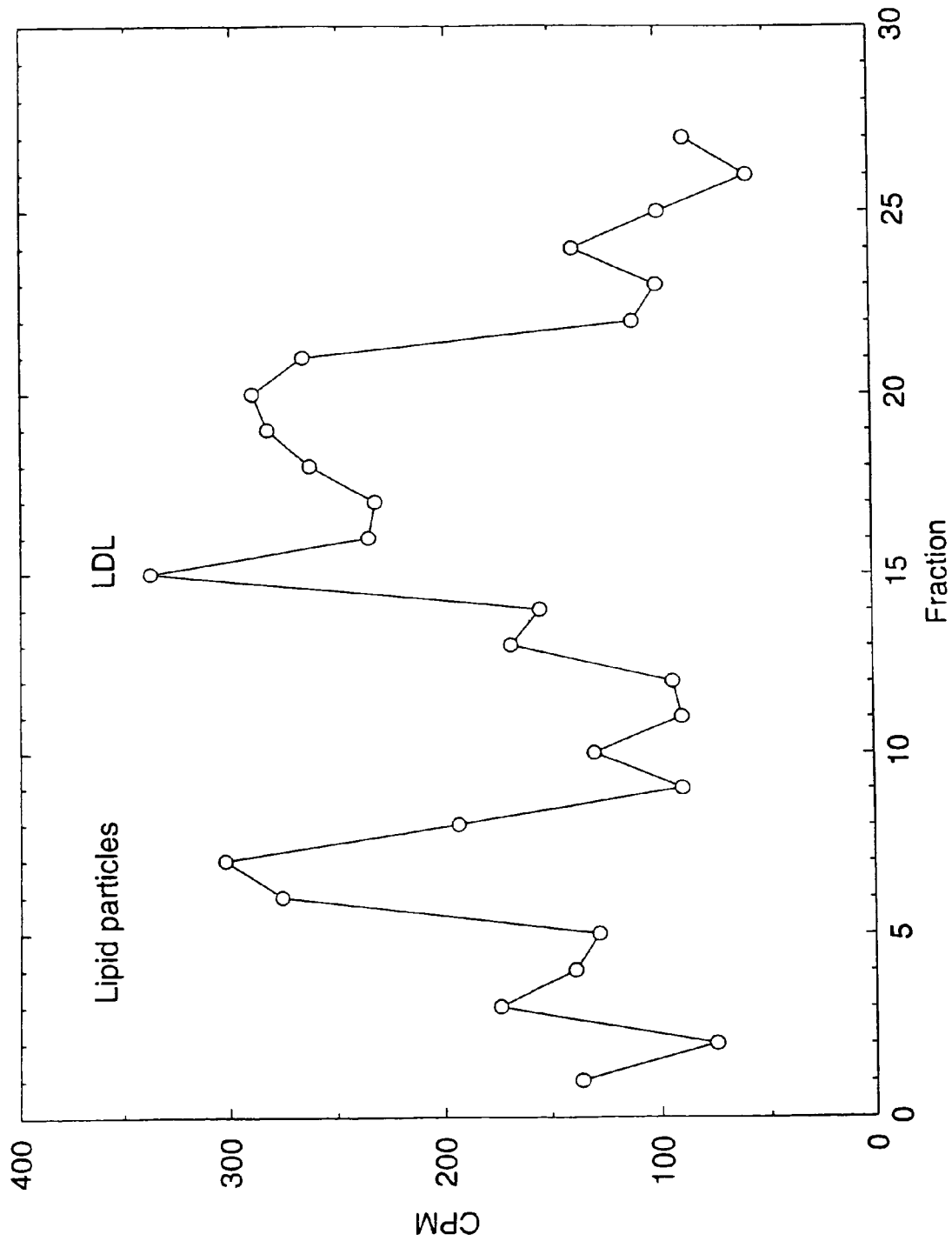
FIG. 1: Potassium bromide density gradient profile of radiolabeled lipids and LDL.

As used herein, the term "artificial LDL particle" means a structure comprising a spherical phospholipid monolayer and a solid lipid core.

As used herein, the term "liposome" means a structure comprising a spherical lipid bilayer and an aqueous core.

As used herein, the term "uptake specificity" refers to the ratio of artificial LDL particle uptake to lipid particle (same as artificial LDL particle except apoprotein is not included in outer phospholipid monolayer) uptake in brain and liver. The uptake of artificial LDL particles and lipid particles is measured in both brain and liver two hours after injection into Sprague-Dawley rats, as described herein. The uptake specificity is calculated by dividing the ratio of artificial LDL particle uptake to lipid particle uptake in brain by the ratio of artificial LDL particle uptake to lipid particle uptake in liver.

As used herein, the term "serum stability" means the length of time at least 75% of the injected artificial LDL particle remains in the plasma.

As used herein, the terms "apolipoprotein" and "apoprotein" mean a protein associated with the phospholipid monolayer of lipoproteins, including but not limited to ApoA; ApoB; ApoC; ApoD; ApoE; and all isoforms of each.

As used herein, the term "ApoE" means one or more of the isoforms of ApoE, including but not limited to ApoE2, ApoE3 and ApoE4.

As used herein, the term "ApoB" means one or more of the isoforms of ApoB, including but not limited to ApoB48 and ApoB-100.

As used herein, the term "outer phospholipid monolayer" means a monolayer comprising at least one phospholipid where the phosphate head groups of the phospholipids are oriented outwardly and the fatty-acyl chains are oriented inwardly toward the solid lipid core. Phospholipids include but are not limited to phosphatidic acid, phosphatidylcholine, phosphatidylethanolamine, phosphatidylserine, phosphatidylglycerol, and the like.

As used herein, the term "solid core" means that portion of an artificial LDL particle enclosed by a spherical phospholipid monolayer. The solid core may comprise one or more lipids, including but not limited to triacylglycerols, cholesterol, cholesterol esters, fatty-acyl esters, and the like. As used herein, the term "cholesterol esters" refer to cholesterol esterified with a saturated fatty acid, including but not limited to myristate, palmitate, stearate, arachidate, lignocerate, and the like, or an unsaturated fatty acid, including but not limited to palmitoleate, oleate, vaccenate, linoleate, linolenate, arachidonate, and the like.

As used herein, the term "therapeutic agent" means therapeutically useful amino acids, peptides, proteins, nucleic acids, including but not limited to polynucleotides, oligonucleotides, genes and the like, carbohydrates and lipids. The therapeutic agents of the present invention include neurotrophic factors, growth factors, enzymes, antibodies, neurotransmitters, neuromodulators, antibiotics, antiviral agents, antifungal agents and chemotherapeutic agents, and the like. The therapeutic agents of the present inventions include drugs, prodrugs and precursors that can be activated when the therapeutic agent is delivered to the target tissue.

As used herein, the term "pharmaceutically acceptable carrier" means a chemical composition or compound with which an active ingredient may be combined and which, following the combination, can be used to administer the active ingredient to a subject. As used herein, the term "physiologically acceptable" ester or salt means an ester or salt form of the active ingredient which is compatible with any other ingredients of the pharmaceutical composition, which is not deleterious to the subject to which the composition is to be administered. As used herein, "pharmaceutically acceptable carrier" also includes, but is not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

As used herein, "an effective amount" is an amount sufficient to produce a therapeutic response.

Properties of LDL Particles and Apoproteins

The present invention relates to the discovery that artificial LDL particles efficiently target and deliver substances across the blood-brain barrier by an active receptor-mediated process known as transcytosis. Transcytosis occurs naturally in brain capillary endothelial cells as a means of importing cholesterol and essential fatty acids into the brain. The artificial LDL carrier system of the invention, therefore, provides a means of effectively targeting and delivering drugs to the brain with minimal disruption of the BBB or other undesirable side effects.

Natural LDL particles have an average diameter of about 22 nm. The inner core consists of approximately 150-200 triglyceride molecules and 1500-2000 cholesteryl ester molecules. The surface of the particles contain a monolayer of about 450 phospholipid molecules, 185 molecules of sphingomyelin, and a single molecule of apoprotein, typically ApoB-100 (Hevonoja et al. (2000) *Biochim Biophys Acta* 1488(3): 189-210). Natural LDL particles may also contain about 600 molecules of unesterified cholesterol and smaller amounts of lysophosphatidyl choline, phosphatidylethanolamine, diacylglycerol, ceramide, and phosphatidylinositol, as well as trace amounts of other biological lipids (Hevonoja et al. (2000) *Biochim Biophys Acta* 1488(3): 189-210). Other apoproteins, including ApoE, are found in LDL, VLVL, and HDL, but possess different receptor binding properties (Bradly et al. (1984) *J. Biol. Chem.* 259(23): 14728-35).

The surface of the LDL particle is, therefore, not uniformly covered with apoprotein, but consists of different regions with different physical properties. The apoprotein molecule is responsible for maintaining the structural integrity of the particle and for binding to lipoprotein receptors in the liver, kidney, and at the blood-brain barrier. Apoproteins undergoes structural changes that depend on the state of the lipid constituents (Mims et al. (1990) *Biochemistry* 29(28): 6639-47).

Apoprotein E (ApoE) is a protein involved in cholesterol transport and plasma lipoprotein metabolism throughout the body. In peripheral cells, ApoE influences cellular concentrations of cholesterol by directing its transport. In neurons, changes in cholesterol levels influence the phosphorylation status of the microtubule-associated protein tau at the same sites that are altered in Alzheimer's disease. ApoE has three major isoforms: ApoE4, ApoE3, and ApoE2, which differ by single amino acid substitutions. ApoE3 is the normal isoform, while ApoE4 and ApoE2 are dysfunctional. ApoE2 is associated with type-III hyperlipoproteinemia. ApoE4 is associated with increased risk for atherosclerosis and Alzheimer's disease, impaired cognitive function, and reduced neurite outgrowth. Except for age, ApoE4 is the most important risk factor in sporadic Alzheimer's disease. ApoE4 may have toxic effects that depend on calcium (Veinbergs et al. (2002) *J. Neurosci. Res.* 67(3): 379-87), but its main effect appears to be to impair clearance of beta-amyloid by ApoE3 (Holtzman et al. (2001) *J. Mol. Neurosci.* 17(2): 147-55). This has been found to occur at the blood-brain barrier (Shibata et al. (2000) *J. Clin. Invest.* 106(12): 1489-99), and therefore could be an important therapeutic application.

Artificial LDL Particle Preparation

In a preferred embodiment, the artificial LDL particles of the invention comprise a mixture of egg yolk phosphatidyl choline (EYPC), cholesterol oleate, and ApoE3. The component lipids form solid particles that consist of three layers (Hevonoja et al. (2000) *Biochim. Biophys. Acta* 1488: 189-210): a solid lipid core containing cholesterol, cholesterol esters, and the active pharmacological agent, which can be either unconjugated or conjugated to the cholesterol; a middle interfacial layer, containing a mixture of fatty acid chains of phosphatidyl choline; and a surface layer, containing phospholipid headgroups and ApoE3.

The solid core and the presence of ApoE3, distinguishes the LDL particles of the invention from liposomes, which consist of a spherical lipid bilayer surrounding an aqueous core and are unstable. In addition, the LDL particles are made of natural, non-immunogenic constituents which distinguishes them from artificial nanoparticles, molecular or chemical conjugates, or colloidal suspensions. The ApoE3 binds to specific receptors on capillary endothelial cells that transport the entire particle across the junction by the active cell-mediated process of transcytosis. Once inside the brain, the therapeutic agent is naturally released from the LDL particle as the cholesterol and phospholipids are gradually assimilated and utilized by the brain.

Although the lipid components stated above are preferred, this invention contemplates that other lipids, for example, LDL particles of different lipid composition, including chemically-modified lipids, or admixtures of other naturally occurring lipophilic molecules could work equally as well. One skilled in the art would understand that modifications may be made to adapt the LDL carrier system for a specific therapeutic agent or therapeutic application.

Preferably, the LDL particles are prepared with artificial LDL and cloned ApoE3. This greatly facilitates efficient and stable incorporation of the therapeutic agent into the lipid center of the LDL, and avoids problems with antigenicity due to possible post-translationally modified, variant, or impure ApoE3 protein purified from human donors. It also avoids possible inadvertent contamination of the ApoE3 or lipids with blood-borne diseases such as HIV or other viruses. Such contamination is always a serious drawback of using human-derived material.

In a preferred embodiment, the present invention relates to a modified microemulsion method of preparing artificial LDL particles comprising the steps of suspending the lipids, containing conjugated or unconjugated drug, in a phosphate buffered saline (PBS) solution, and sonicating the solution for 1 hour under a nitrogen atmosphere at 54° C. using a sonicator capable of delivering at least approximately 25 watts (18 µm amplitude of the probe at 22 kHz). This power level is important for creating LDL particles of an appropriate size to facilitate transport across the BBB, preferably less than 50 nm in diameter, and more preferably less than 30 nm in diameter. The sample containing the LDL particles is maintained at a constant temperature, preferably between about 53 and 56° C., by use of a water-jacketed sonication chamber. Following sonication, the lipid solution is incubated with ApoE and the lipoprotein particles that are produced are separated by ultracentrifugation in a potassium bromide (KBr) step gradient at 285,000 g. The KBr is then removed by dialysis against PBS. The particles can be stored at 4° C. for later use, preferably up to two weeks.

One skilled in the art would recognize that various aspects of the method may be substituted. For example, other suitable density gradients, such as cesium chloride or sucrose, may be substituted. In an alternative embodiment, the LDL particles of the invention can be isolated by size exclusion chromatography, electrophoresis, or other means instead of centrifugation.

The method of preparation described herein produce drug-containing LDL particles that are of an appropriate size to cross the BBB and maintain the activity and structural stability of labile co-incorporated molecules. For delivery to the brain, the LDL particles should generally be less than 50 nm in size, with a preferred range of 20 to 30 nm in diameter.

In another preferred embodiment, the LDL particles of the invention comprise a mixture of EYPC, cholesterol oleate, and ApoE3 present at a ratio of 0.02 to 0.2 grams per gram of liposomes and provide efficient incorporation of the therapeutic agent and transcytosis across the BBB. In a more preferred embodiment, the range is 0.08 to 0.12 grams per gram of liposomes. More preferably, the molar ratio of EYPC to cholesterol oleate to ApoE3 is 23:2:2 on a weight basis.

In yet a further embodiment of the invention, the LDL-based carrier system may contain additional targeting molecules co-incorporated in the surface layer to further facilitate transport and delivery of agents to the brain. By way of example, oxidized derivatives of cholesterol (oxysterols) including cholesterol hydroperoxides, cholesterol epoxides, and hydroxycholesterol derivatives may also be used to improve uptake. The LDL particles may also incorporate other apoproteins such as ApoB or ApoE4.

The present invention also relates to the incorporation of one or more of a wide variety of substances including therapeutic agents to treat a variety of brain diseases or disorders. One of the advantages of the LDL carrier system is the ability to deliver safety and naturally a broad variety of drug classes, including those that are chemically unstable, highly reactive, or readily hydrolyzed in aqueous solution.

The list of possible agents include, but are not limited to: neurotrophic factors, such as NGF or the neurotrophic fragments produced from amyloid precursor protein, to treat brain injury and neurodegenerative diseases; enzymes, such as phenylalanine hydroxylase, to replace those lost through genetic defects; enzymes, such as tyrosine hydroxylase and DOPA decarboxylase, to regenerate dopamine that is lost in Parkinson's disease; enzyme activators or inhibitors to restore lost biosynthetic function: antibiotics, such as tetracycline, for treating infectious diseases; neurotransmitters and neuromodulators for treating pain, or conditions including disorders of movement, cognition, and behavior; chemotherapeutic agents and anti-AIDS drugs, such as etoposide, ribavirin, or antihistamines, such as loratadine, fexofenadine, or certirizine (Zyrtec®), for treating brain tumors or other conditions with agents that do not reach the brain in sufficient amounts when tolerable doses are administered systemically; diagnostic agents, including contrast media like gadolinium derivatives, iohexol, or ioxaglate, or agents that are currently not used because of poor penetration into the brain upon systemic administration; therapeutic or diagnostic proteins such as antibodies, engineered and natural; and therapeutic sequences encoding genes or proteins, or portions thereof, comprised of DNA, RNA, or amino acids that can be introduced non-invasively across the BBB.

The amount of therapeutic agent present in the LDL carrier will vary widely, depending on the type of molecule. For optimal incorporation in the LDL carrier, the amount of therapeutic agent should be less than 0.1 mol/mol cholesterol. It is expected that higher levels may destabilize the LDL particles. This invention further contemplates that multiple drugs or additional agents may be present in the same particle.

In one embodiment, no covalent modification of the active substance is required for incorporation in the LDL particle of the invention, provided the substance is sufficiently hydrophobic to remain as a microemulsion with cholesterol. This is true of most neutral and moderately-charged molecules.

In another embodiment, if, for example, a therapeutic agent is highly charged, like DNA or a peptide, or alternatively, to prevent diffusion, the agent can be covalently linked to cholesterol. In a preferred embodiment, the linkage is made with an ester bond, which would allow the agent to be released by the ubiquitous esterases found in brain tissue (Yordanov et al., (2002) *J. Med. Chem.* 45(11): 2283-8; Yang et al. (1995) *Pharm. Res.* 12(3): 329-36). Alternatively, one skilled in the art would be able to select other modes of attachment which would work equally as well, among them, illustratively, covalent attachment to phosphatidyl choline, some other lipophilic compound, or ApoE itself.

As state above, the LDL particles of the invention have several advantages when compared to other carriers such as pegylated liposomes, nanoparticles, and similar artificial substances. The LDL particles of the invention are made of normal constituents of blood plasma, bind to their natural receptor, and are transported by normal pathways into the cells as part of the brain's natural requirement for exogenous essential fatty acids. Therefore, their toxicity is significantly lower than polymer-based carriers and agents that disrupt cell membrane integrity. A current method used for delivering drugs to the brain is osmotic disruption of the BBB with mannitol. Disrupting the BBB, however, has serious drawbacks, among them the fact that it allows toxins and even viruses to enter the brain along with the desirable therapeutic agent which can have serious collateral effects.

Figure 4:
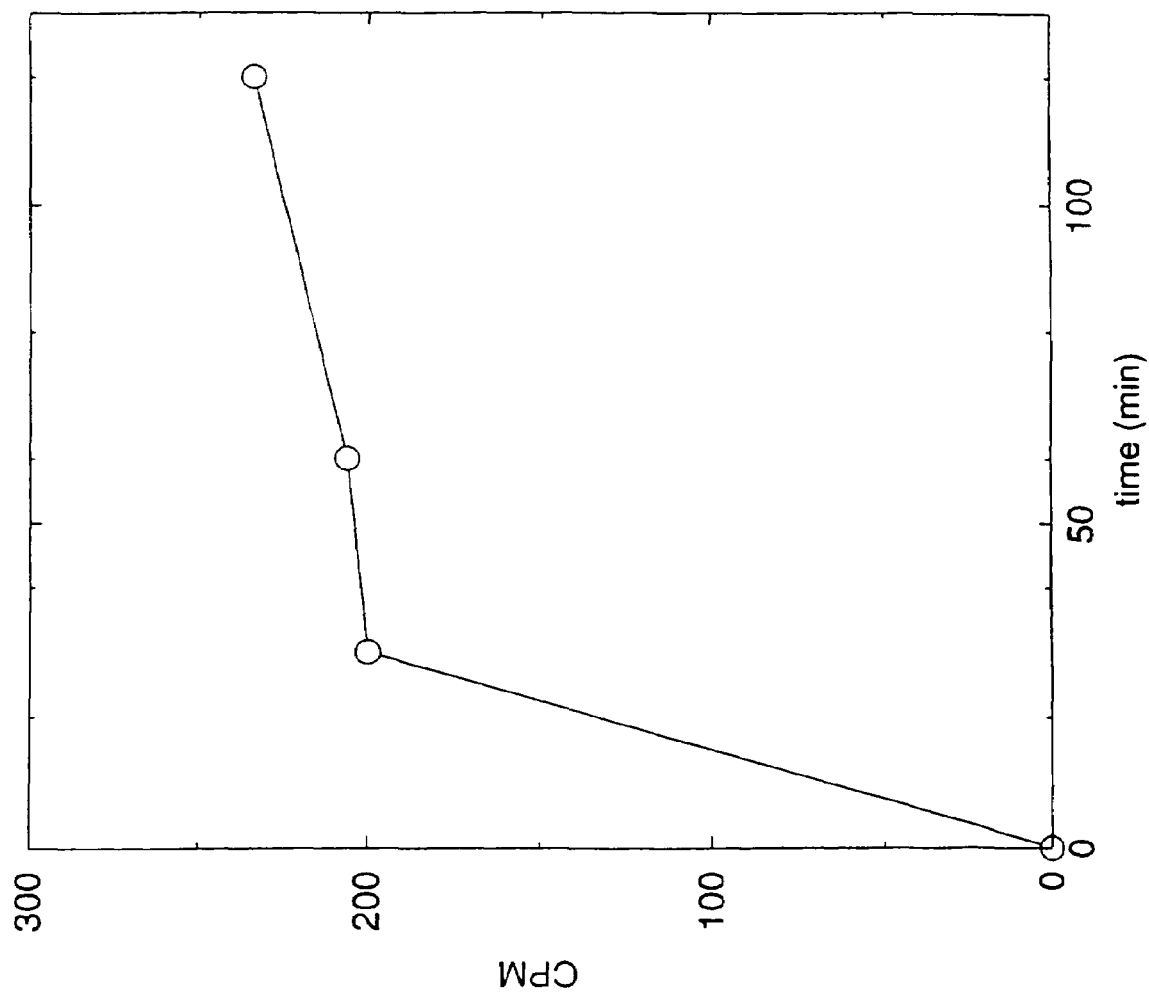
FIG. 4: Time course of plasma levels of $^{14}$C-Labeled LDL particles.

The artificial LDL carrier system of the invention also provide the advantage that they remain at high levels in plasma for at least two hours (FIG. 4). This is important in maintaining a sufficient effective plasma concentration (often referred to as "area under the plasma concentration curve" or AUC) for adequate uptake and delivery of substances to the brain.

By specifically targeting brain tissue, as shown in Example 3, the artificial LDL particles of the invention significantly increase the therapeutic efficacy of drugs, because the drugs are much less likely to be taken up by the liver and inactivated by detoxification pathways, including inactivation by liver enzymes such as P450.

Compositions Comprising Artificial LDL Particles

The LDL particles of the invention may be formulated in a variety of ways depending on the type of brain disease to be treated. The invention therefore includes within its scope pharmaceutical compositions comprising at least one drug-containing LDL particle complex formulated for use in human or veterinary medicine. Such compositions may be presented for use with pharmaceutically-acceptable carriers or excipients, optionally with supplementary medicinal agents. Conventional carriers can also be used with the present invention. Acceptable carriers include, but are not limited to, glucose, saline, and phosphate buffered saline.

Following treatment to remove free therapeutic agent or other non-incorporated molecules, the LDL particle suspension is brought to a desired concentration in a pharmaceutically acceptable carrier for administration to a patient. Because the LDL particles are too large to be efficiently absorbed parenterally, compositions are intended for intravenous use, but conceivably may also be administered intramuscularly or intraarterially, or even parenterally or orally given appropriate modifications.

Thus, this invention provides compositions for administration targeted to the BBB which comprise a solution of a selected active agent contained in an LDL particle and a pharmaceutically acceptable carrier, preferably an aqueous carrier. The resulting compositions may be sterilized and packaged for use in a kit, or filtered under aseptic conditions and lyophilized. Kits for intravenous administration containing a lyophilized preparation may also include a sterile aqueous solution for mixing prior to administration.

The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of the LDL particles in these formulations can vary widely, i.e. from less than about 0.5%, usually at or at least about 1%, to as much as 5 to 10% by weight. Additional methods for preparing intravenously administrable, LDL particle formulations will be known to those skilled in the art. Such methods are described in detail in, for example, Goodman & Gilman, The Pharmacological Basis of Therapeutics by Joel G. Hardman (Editor), Lee E. Limbird McGraw-Hill Professional; ISBN: 0071354697; 10$^{th}$ edition (Aug. 13, 2001).

Therapeutic Methods of Using Artificial LDL Carriers

In a further embodiment, the artificial LDL particles may be administered to a mammalian host in need of treatment to effectively deliver agents across the BBB to the brain. For use in therapy, an effective amount of drug-containing LDL particles can be administered to a subject by any mode allowing LDL particles to be taken up by the capillary endothelial cells.

In clinical applications, the LDL particle delivery system significantly enhances the therapeutic efficacy of drugs for uses such as the treatment of Alzheimer's disease, Parkinson's disease, and brain cancer. For example, a neurotrophic factor such as nerve growth factor could be incorporated into the LDL particles, enabling the peptide to be taken up into the brain. This would cause the growth of new nerve processes that could be beneficial in a number of neurodegenerative diseases. As described herein, those skilled in the art would recognize that a broad variety of alternative clinical applications exist using the LDL carrier system of the invention.

Cholesterol-Conjugates of Therapeutic Agents.

Cholesterol is a relatively chemically-inactive molecule. Consequently, cholesterol must be activated prior to reacting the cholesterol with an amine-containing therapeutic agent. For example, cholesterol may be activated by a reaction with a cyclic anhydride such as phthalic or succinic anhydride that produces a phthalate or succinate ester which contains a carboxyl group. The carboxyl group is then activated by reaction with pentafluorophenol and then reacted with diisopropylcarbodiimide to create an amide linkage with an amine-containing therapeutic agent. The resulting product is a cholesterol-therapeutic agent conjugate wherein the therapeutic agent is conjugated to cholesterol through an ester linkage. The cholesterol-therapeutic agent conjugate is sufficiently lipophilic to allow incorporation into the artificial LDL particles of the present invention. Also, since the preferred linkage is an ester bond, the therapeutic agent can be released from the cholesterol moiety by the action of ubiquitous endogenous esterases. Thus, the release of the therapeutic agent from the conjugate is not dependent on the harsh conditions and action of non-specific peptidases found in lysosomes. Although the preferred linkage between cholesterol and a therapeutic agent is an ester bond, the present invention contemplates other linkages, including but not limited to ether, amide and peptide bonds.

Alternatively, an amine- or hydroxyl-containing therapeutic agent may be conjugated to thiocholesterol by reaction of thiocholesterol, a therapeutic agent and a bifunctional cross-linking reagent such as, but not limited to, PMPI. The resultant conjugate is a conjugate of cholesterol and a therapeutic agent linked by a thioether linkage. If the therapeutic agent contains an amino group, it may be conjugated to thiocholesterol using one of the many commercially-available bifunctional crosslinking agents, including but not limited to succinimidyl 4-[N-maleimidomethyl]cyclohexane-1-carboxylate.

Once formed, the cholesterol-therapeutic agent conjugates may be mixed with unconjugated cholesterol oleate, phospholipids, lipoproteins, as described herein, thereby producing the artificial LDL particles of the present invention.

Each reference cited above is incorporated herein by reference, in its entirety.

EXAMPLES

The following Examples serve to illustrate further the present invention and are not to be construed as limiting its scope in any way.

Example 1

Purification of Full-Length Apoprotein E (ApoE)

DMPC (1,2-dimyristoyl-sn-glycero-3-phosphocholine) from Avanti Polar Lipids, Inc. is suspended in benzene at a concentration of 100 mg/ml in a glass tube and sonicated using bench top sonicator. The DMPC suspension is shell-frozen and lyophilized overnight, then resuspended in 30 ml standard buffer (10 mM Tris-HCl. pH 7.6. 0.15M NaCl, 1 mM EDTA. 0.0005% $NaN_3$) to make 10-20 mg/ml DMPC and transferred to a plastic 50 ml conical tube. The tube is placed in a water bath and sonicated using a sonicator with a microtip for four 10 min intervals, interspersed with 2-3 min cooling. Sonication is repeated until the solution becomes nearly transparent. The sonicated DMPC is then centrifuged at 2000 rpm for 20 minutes to remove any titanium that may have sloughed off during sonification.

Bacterial cells expressing cloned ApoE are collected by centrifugation and sonicated on ice in a Branson Sonifier with a large tip, using four periods of high intensity sonification for 30 sec separated by 2 min cooling intervals. The sonicated suspensions are centrifuged at 39.000×g for 20 min at 4° C. to remove cell debris and the supernatant is combined with DMPC at 100 mg per liter of original culture medium. The mixture is incubated in a water bath at 24° C. (which is the transition temperature for DMPC) overnight.

The density of the DMPC-ApoE mixture is then raised to 1.21 g/ml by addition of solid KBr and centrifuged in a step gradient (1.21, 1.10, and 1.006 g/ml) overnight at 55,000 rpm in a 60 Ti Beckman fixed-angle rotor at 15° C. The white band near the top of the tube containing free DMPC is discarded, and the ApoE-DMPC complex below it, floating at density of 1.009 g/ml, is removed. The presence of ApoE is confirmed by gel electrophoresis. Appropriate fractions are then dialyzed against 0.1M $NH_4HCO_3$ and 0.0005% $NaN_3$ at 4° C. against three changes of buffer.

The protein is then digested with thrombin to remove the polyhistidine tag left by the vector. Activated thrombin is mixed with the protein at a ratio of 1:500 thrombin:ApoE, w:w, and incubated at 37° C. for at least 1 hr and aliquots are analyzed by gel electrophoresis to ensure that the protein is completely cleaved. Because of the presence of two cleavage sites, incomplete cleavage would result in a second band with a higher molecular weight. Once complete cleavage has been demonstrated, beta-mercaptoethanol is added to a 1% final concentration to stop the reaction. The ApoE is then shell frozen ApoE in a 50 ml acid washed tubes and lyophilized overnight.

The ApoE is then washed with 30 ml cold chloroform/methanol (2:1 v/v) and collected by centrifugation at 1500 rpm in a J6 Beckman centrifuge at 4° C. for 10 min. The pellet is resuspended in a small volume of cold methanol and vortexed, and the tube is then filled with cold methanol and centrifuged. This step removes any remaining chloroform. The methanol is poured off, leaving a small amount in the tube which is vortexed to make a paste out of pellet. Five ml of a solution containing 6M guanidine-HCl. 0.1M Tris HCl, pH 7.4, 0.01% EDTA, 1% beta-mercaptoethanol, and 0005% sodium azide, is added and the solution is loaded onto a Sephacryl S-300 column that has been equilibrated with 4M guanidine-HCl, 0.1M Tris-HCl, pH 7.4, 0.1% beta-mercaptoethanol, and 0.0005% $NaN_3$. The protein is eluted with 4M guanidine buffer that contains 0.1% beta-mercaptoethanol and 0.0005% sodium azide. Fractions are dialyzed against 0.1M $NH_4HCO_3$ and 0.0005% $NaN_3$, with four changes of buffer. The purified ApoE is concentrated using YM10 Amicon Centriprep concentrators (Millipore) to a final concentration of 1-2 mg/ml, and stored at −20° C.

Example 2

ApoE Enrichment of LDL-Liposomes

1. Preparation of lipid cake: Egg yolk phosphatidylcholine (25 mg) and cholesterol oleate (2 mg) are dissolved (ratio 12.5:1) in methanol/chloroform (2:3). The solvent is evaporated under nitrogen at 4° C.

2. Preparation of liposomes: The lipid cake is hydrated in 12 ml of 10 mM Tris-HCl buffer, p H 8.0, containing 0.1M potassium chloride previously bubbled under nitrogen gas. The mixture is sonicated for 1 h at 18-um output under nitrogen stream at 54° C. and centrifuge to remove any titanium particles produced during sonication.

3. Preparation of artificial LDL: The liposomes prepared in step 2 are incubated with ApoE protein in a ratio of 1/10 (w/w) protein/lipid for 30 min at 37° C. The liposomes are then purified and concentrated by density gradient ultracentrifugation at 285,000×g for 18 h at 4° C. using a three-layer KCl step gradient with densities of 1.064, 1.019, and 1.006 g/cm$^3$. KBr is added to the liposome solution to raise its density to 1.21 and applied to the bottom of the centrifuge tube. Optiseal tubes (Beckman) are suitable for the ultracentrifugation step. After centrifugation, liposomes are visible as a narrow opalescent layer approximately ¼ of the distance from the top of the tube. This layer is removed and dialyzed overnight at 4° C. against PBS (phosphate-buffered saline) containing 1 mM EDTA. The LDL suspension is stable for at least 7 days and can be stored at −20° C. under argon or nitrogen.

Example 3

Uptake of Artificial LDL Particles in Brain

The $^{14}$C-LDL suspension in PBS, containing approx. 1 mg lipid, was injected into the tail vein of a Sprague-Dawley rat (150 g). At various intervals, blood samples were obtained by cardiac puncture using syringes containing EGTA. Blood plasma, RBCs, and tissues were homogenized in water and the $^{14}$C was measured in a scintillation counter.

Figure 2:
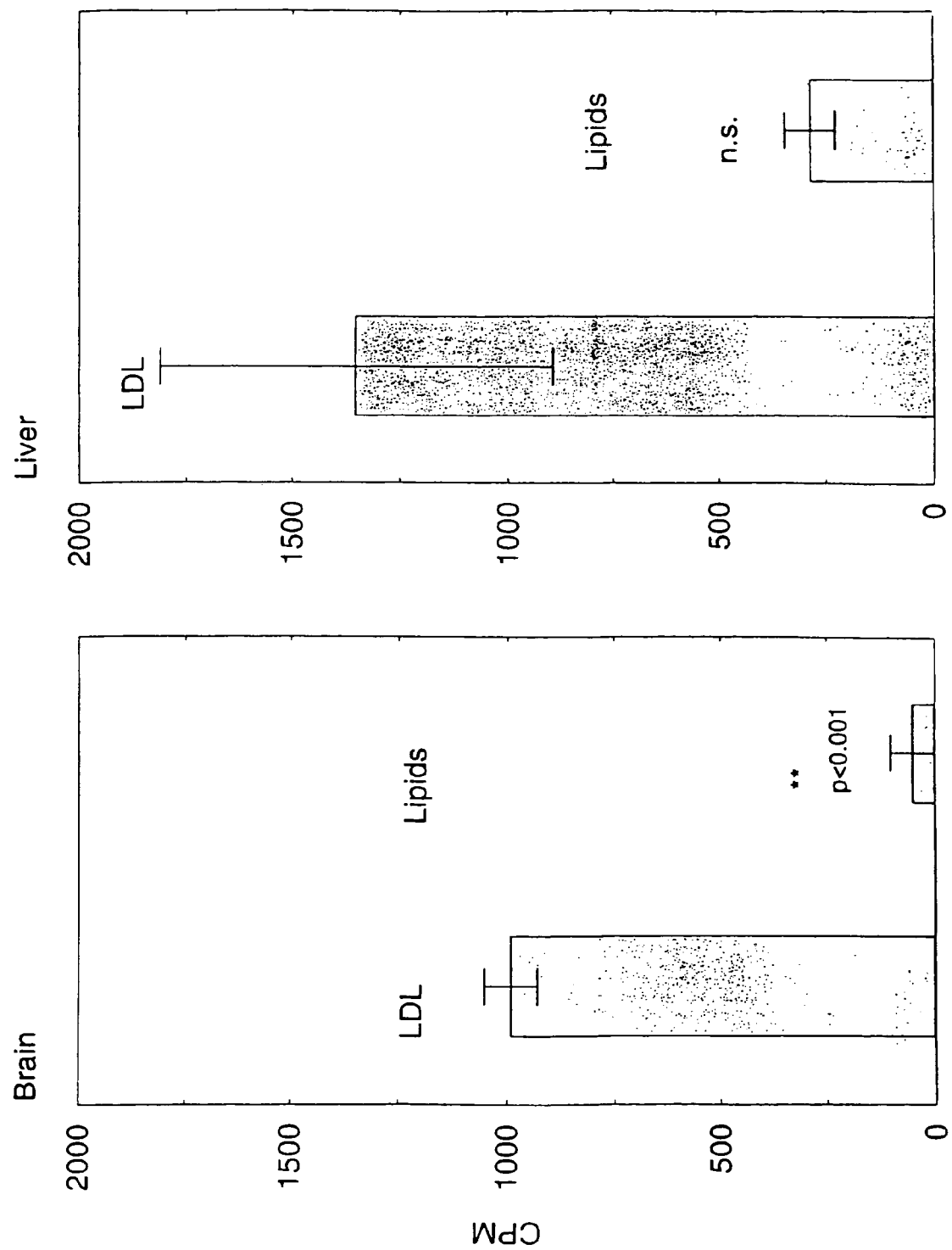
FIG. 2: Uptake of LDL and lipids in brain (left) and liver (right).

FIG. 2 shows the results of uptake of LDL and lipids in brain (left) and liver (right). Male Sprague-Dawley rats were injected intravenously with LDL or lipid particles containing $^{14}$C-cholesterol and radioactivity in brain and liver was measured two hours later. Brain and liver took up 19.8 and 4.7 times more label, respectively, from LDL compared to lipid particles of identical composition except for the presence of ApoE. This indicates that the uptake was caused by transcytosis mediated by the LDL receptor (p(>T)=0.00055).

Figure 3:
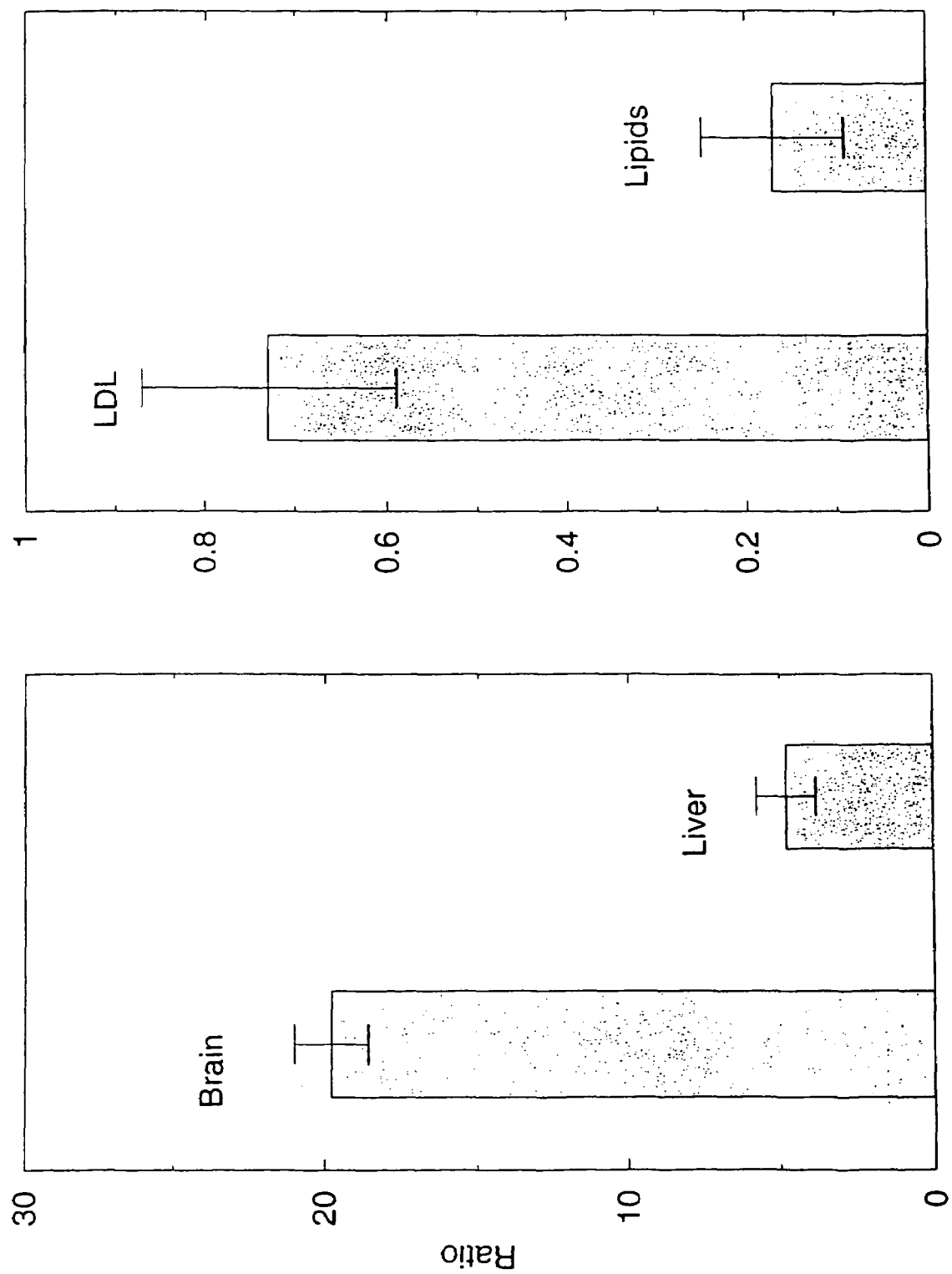
FIG. 3: (Left). Ratio of LDL uptake to lipid particle uptake in brain and liver. (Right). Ratio of brain uptake for LDL and lipid particles.

FIG. 3 (left) shows the ratio of LDL uptake to lipid particle uptake in brain and liver. Brain incorporated a higher percentage of LDL versus lipid particles compared to liver (p(>T)= 0.0003) suggesting a 4-fold greater specificity of LDL for the target organ compared to liver. FIG. 3 (right) shows the ratio of brain uptake to liver uptake for LDL and lipid particles. The brain:liver ratio, another measure of organ specificity, was higher for LDL than for lipid particles, (p(>T)=0.0003). In other words, 5.88 times more lipid particles were taken up by the liver than brain, while only 1.36 times more LDL particles were taken up by the liver than brain (p(>T)=0.034).

FIG. 4 shows the time course of plasma levels of $^{14}$C-labeled LDL particles. Blood $^{14}$C remained constant for at least 2 hours after injection of LDL, indicating that the label was not being removed from circulation by other organs.

Example 4

Conjugation of Primary Amines with $^{14}$C Cholesterol

Preparation of cholesterol-phthalate ester: Cholesterol (1 mg) is evaporated with nitrogen and lyophilized to remove ethanol. The solid is dissolved in a minimum volume THF and transferred to a glass reaction vial. Solid phthalic anhydride (1-2 mg, >4 equiv.) is added, followed by 50 Et$_3$N. The mixture is heated at 1000 for 5 min and ≈20 µl pyridine is added to make suspension clear. The mixture is heated at 100° for 30 min until solution is red and purified on TLC (Silica/UV254 plates) with EtOH/toluene (2:1). The highest dark UV band ($R_F$=0.74) is scraped from the plate and the product eluted with THF (yield: 98=100%).

Activation of carboxyl group with pentafluorophenol: 10 mg of pentafluorophenol (PFP) in THF is added to cholesterol phthalate followed by 5 µl DIIC (diisopropylcarbodiimide). The solution is reacted 1 hr at room temperature (RT) in a reaction vial, and the activated cholesterol-phthalate-PFP is purified by TLC (CHCl$_3$/CH$_3$OH 30:5), and eluted with THF (yield: 100%).

Production of activated amide: Activated cholesterol-phthalate-PFP in THF is evaporated to 10 µl and 2 equiv primary amine dissolved in DMF is added. DMF can cause a side reaction but this is not a problem if excess amine is present. The addition of alcohols such as methanol or ethanol will greatly reduce the yield. Three microliters DIIC are added and the solution is reacted overnight at RT and purified by TLC (CHCl$_3$/CH$_3$OH 30:5) (yield 98%). Importantly, only Silica Gel G-25 UV254 plates (Alltech 809021) were used for purification. Silica gel 60 plates produce a fuzzy indistinct band that impairs purification.

Example 5

Synthesis of Adriamycin-cholesterol (I)

Figure 5:
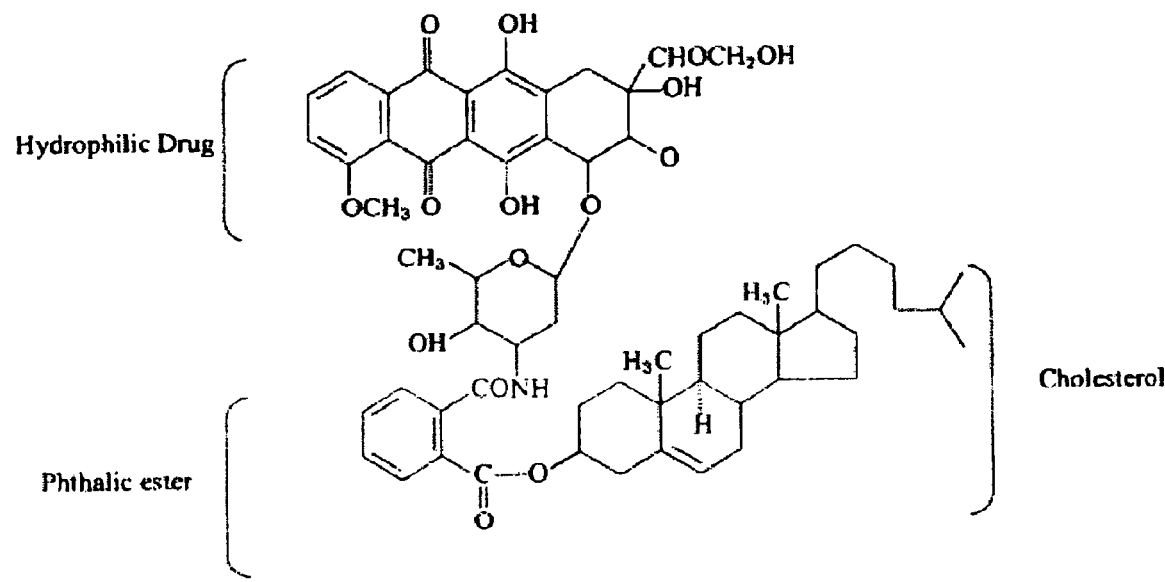
FIG. 5: Chemical structure of a hydrophilic molecule linked to cholesterol via a phthalate ester. The specific hydrophilic molecule shown is adriamycin. Without conjugation, adriamycin alone is too hydrophilic and cannot be incorporated into LDL particles.

Activated cholesterol-phthalate-PFP in THF is evaporated to 10 µl. 2 equivalents of adriamycin dissolved in DMF is added. Side reactions with DMF may be reduced by using excess amine. The addition of alcohols such as methanol or ethanol will greatly reduce the yield. Three microliters DIIC are added and the solution is reacted overnight at RT and purified by TLC (CHCl$_3$/CH$_3$OH 30:5) (yield 95%). This band contains the adriamycin-DIIC conjugate and product. The cholesterol-adriamycin conjugate can be isolated by C$_{18}$-reverse-phase HPLC in 100% CH$_3$OH (flow rate=0.5 ml/min, detection=A$_{471}$). The product elutes at 4.7 min, about halfway between cholesterol and adriamycin. Overall yield: 95%. The structure of the adriamycin-cholesterol conjugate (I) is depicted in FIG. 5.

Example 6

Conjugation of Hydroxy-containing Compounds with $^{14}$C Cholesterol

N-[p-maleimidophenyl]isocyanate (PMPI)(5 mg) is mixed with 1 equiv. of a hydroxy-containing compound in 200 µl DMSO and reacted 30 min at room temperature. Thiocholesterol (6.4 mg) is added. The mixture is incubated for 120 min at room temperature and the product isolated by thin-layer chromatography using Silica Gel G UV 254 plates precoated with 0.1M EDTA pH 8.0, with EtOH/H2O 1:1 as the solvent.

Example 7

Synthesis of Tetracycline-cholesterol (II)

Figure 6:
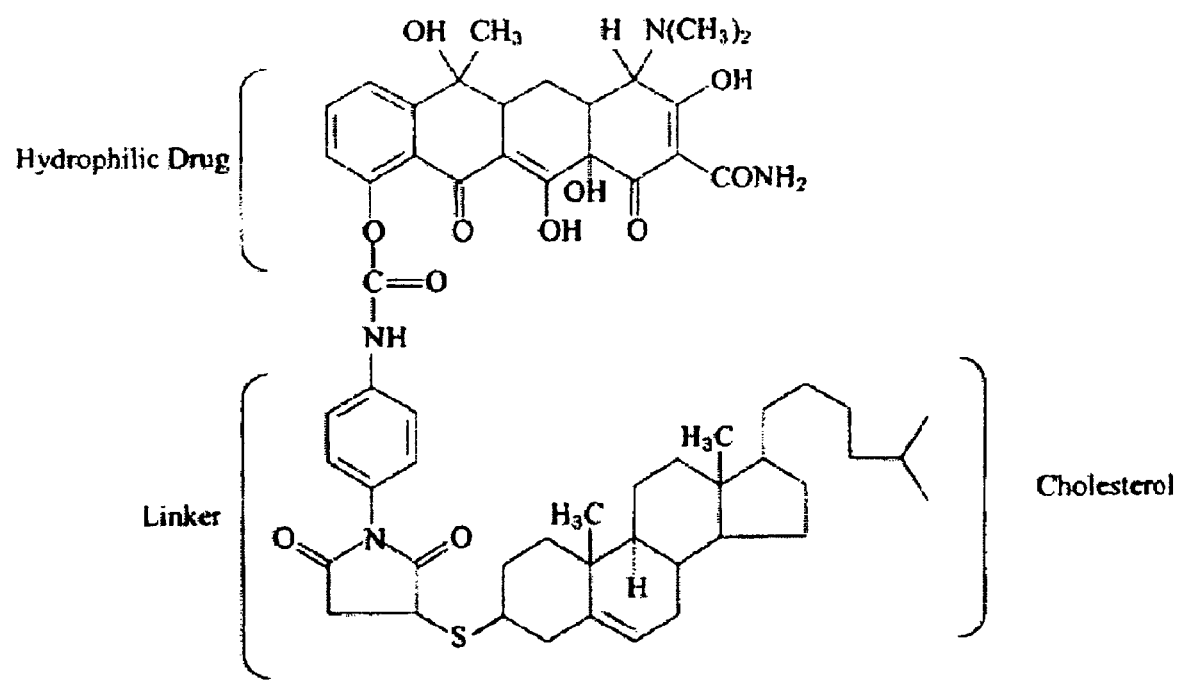
FIG. 6: Chemical structure of a hydrophilic molecule linked to cholesterol via a thioether ester. The specific hydrophilic molecule shown is tetracycline. Without conjugation, tetracycline alone is too hydrophilic and cannot be incorporated into LDL particles.

Tetracycline is lyophilized to remove any solvent and 2.2 mg tetracycline in 200 µl DMSO is mixed 5 mg PMPI and reacted 30 min at room temperature. Thiocholesterol (6.4 mg) is added. The mixture is incubated for 120 min at room temperature and the product isolated by thin-layer chromatography using Silica Gel G UV 254 plates precoated with 0.1M EDTA pH 8.0, with EtOH/H2O 1:1 as the solvent. The structure of the tetracycline-cholesterol conjugate (II) is depicted in FIG. 6.

REFERENCES

Each of the reference listed below is incorporated herein by reference in its entirety.

1. Alyaudtin et al. (2001) Interaction of poly(butylcyanoacrylate) nanoparticles with the blood-brain barrier in vivo and in vitro. *J. Drug Target* 9(3):209-21.
2. Bickel et al. (1993) Delivery of peptides and proteins through the blood brain barrier. *Adv Drug. Del. Rev.* 10: 205-245.
3. Bradley et al. (1984) Low-density lipoprotein receptor binding determinants switch from apoprotein E to apoprotein B during conversion of hypertriglyceridemic very-low-density lipoprotein to low-density lipoproteins. J Biol Chem 259(23):14728-35.
4. Goodman & Gilman, The Pharmacological Basis of Therapeutics by Joel G. Hardman (Editor), Lee E. Limbird McGraw-Hill Professional; ISBN: 0071354697; 10$^{th}$ edition (Aug. 13, 2001).
5. Hevonoja et al. (2000) Structure of low density lipoprotein (LDL) particles: basis for understanding molecular changes in modified LDL. *Biochim Biophys Acta* 1488(3): 189-210.
6. Holtzman (2001) Role of ApoE/Abeta interactions in the pathogenesis of Alzheimer's disease and cerebral amyloid angiopathy, *J Mol Neurosci* 17(2): 147-55.
7. Huwyler et al. (1996) Brain drug delivery of small molecules using immunoliposomes. *Proc. Nat'l. Acad. Sci. USA* 93: 4164-14169.
8. Kang et al. Brain delivery of biotin bound to a conjugate of neutral avidin and cationized human albumin. *Pharm. Res. ll,* 1257-1264.
9. Kang et al. (2000) Stability of the disulfide bond in an avidin-biotin linked chimeric peptide during in vivo transcytosis through brain endothelial cells. *J Drug Target* 8(6):425-34.
10. Kreuter et al. (2002) Apolipoprotein-mediated transport of nanoparticle-bound drugs across the blood-brain barrier. *J Drug Target* 10(4):317-25.
11. Mims et al. (1990) Effect of particle size and temperature on the conformation and physiological behavior of apolipoprotein E bound to model lipoprotein particles. *Biochemistry* 29(28):6639-47.
12. Pardridge (1990) CNS drug design based on principles of blood-brain barrier transport. *J. Neurochem* 70: 1781-2.
13. Pardridge et al. (1986) Blood-brain barrier: interface between internal medicine and the brain. *Ann Intern Med* 105(1): 82-95.
14. Reinhardt et al. (1994) Insulin-like growth factors cross the blood-brain barrier. *Endocrinology* 135(5): 1735-1761.
15. Rigotti et al. (1995) The class B scavenger receptors SR-B1 and CD36 are receptors for anionic phospholipids. *J. Biol. Chem.* 270, 16221-4.
16. Shibata et al. (2000) Clearance of Alzheimer's amyloid-ss (1-40) peptide from brain by LDL receptor-related protein-1 at the blood-brain barrier. *J. Clin. Invest.* 106(12): 1489-99.
17. Veinbergs et al. (2002) Neurotoxic effects of apolipoprotein E4 are mediated via dysregulation of calcium homeostasis. *J Neurosci Res* 67(3): 379-87.
18. Witt et al. (2000) Insulin enhancement of opioid peptide transport across the blood-brain barrier and assessment of analgesic effect. *J Pharmacol Exp Ther* 295(3):972-8.
19. Wu et al. (2002) Pharmacokinetics and brain uptake of biotinylated basic fibroblast growth factor conjugated to a blood-brain barrier drug delivery system. *J Drug Target* 10(3): 329-45.
20. Yang et al. (1995) Soft drugs. XX. Design, synthesis, and evaluation of ultra-short acting beta-blockers. *Pharm Res* 12(3): 329-36.
21. Yordanov et al. (2002) Acyl-protected hydroxylamines as spin label generators for EPR brain imaging. *J. Med. Chem.* 45(11): 2283-8.
22. Dehouck et al. (1977) A new function for the LDL receptor: Transcytosis of LDL across the blood-brain barrier. *J. Cell. Biol.* 138(4):877-89.
23. Versluis et al. (1998) Synthesis of a lipophilic daunorubicin derivative and its incorporation into lipidic carriers developed for LDL receptor-mediated tumor therapy. *Pharm. Res.* 15(4):531-537.
24. Versluis et al. (1998) Low-density lipoprotein receptor-mediated delivery of a lipophilic daunorubicin derivative to B16 tumors in mice using apolipoprotein E-enriched liposomes. *B.r.J. Cancer* 78(12): 1607-14.
25. Versluis et al. (1999) Stable incorporation of a lipophilic daunorubicin prod rug into apolipoprotein E-exposing liposomes induces uptake of prod rug via low-density lipoprotein receptor in vivo. *J. Pharmacol. Exp. Ther.* 289(1): 1-7.
26. Annunziato et al. (1993) p-Maleimidophenyl isocyanate: A novel heterobifunctional linker for hydroxyl to thiol coupling. *Bioconjugate Chem.* 4:212-218.
27. Demeule et al. (2002) High transcytosis of melanotransferrin (P97) across the blood-brain barrier. *J. Neurochem* 83(4):924-33.

We claim:

1. An artificial low-density lipoprotein (LDL) particle comprising artificial LDL, an outer phospholipid monolayer and a solid lipid core, wherein the outer phospholipid monolayer comprises at least one cloned apolipoprotein and the solid lipid core contains at least one therapeutic agent, wherein the at least one cloned apolipoprotein is apolipoprotein E.

2. The artificial LDL particle of claim 1, wherein the at least one apolipoprotein is ApoE3.

3. The artificial LDL particle of claim 2, wherein the outer phospholipid monolayer further comprises one or more oxysterols and/or an additional apolipoprotein selected from the group consisting of ApoB and ApoE4.

4. The artificial LDL particle of claim 1, wherein the at least one therapeutic agent is selected from the group consisting of: amino acids, peptides, proteins, carbohydrates, drugs, and lipids.

5. The artificial LDL particle of claim 4, wherein the therapeutic agent is selected from the group consisting of: neurotrophic factors, growth factors, enzymes, antibodies, neurotransmitters, neuromodulators, antibiotics, antiviral agents, antifungal agents and chemotherapeutic agents.

6. The artificial LDL particle of claim 1, wherein the outer phospholipid monolayer comprises phosphatidylcholine.

7. The artificial LDL particle of claim 1, wherein the particle has a diameter between about 15 and 50 nm.

8. The artificial LDL particle of claim 1, wherein the particle has a diameter between about 20 and 30 nm.

9. The artificial LDL particle of claim 1, wherein the particle has a density between about 1.00 and 1.07 g/ml.

10. The artificial LDL particle of claim 1, wherein the particle has a density between about 1.02 and 1.06 g/ml.

11. The artificial LDL particle of claim 1, wherein the particle has a serum stability of at least two hours.

12. The artificial LDL particle of claim 1, wherein the particle is transported across the blood-brain barrier (BBB) by transcytosis.

13. The artificial LDL particle of claim 1, wherein the particle has at least a 3-fold greater uptake specificity for brain compared to liver.

14. The artificial LDL particle of claim 1, wherein the at least one therapeutic agent is a conjugate formed between cholesterol and adriamycin.

15. The artificial LDL particle of claim 1, wherein the at least one therapeutic agent is a conjugate formed between cholesterol and tetracycline.

16. An artificial LDL particle for delivery of an agent across the blood-brain barrier comprising artificial LDL, an outer phosphatidylcholine monolayer, a solid lipid core comprising fatty acyl-cholesterol esters and a therapeutic agent, and cloned ApoE in the outer monolayer.

17. The artificial LDL particle of claim 16, wherein the solid lipid core further comprises cholesterol.

18. The artificial LDL particle of claim 16, wherein the ApoE in the outer monolayer is ApoE3.

19. A composition for delivery of an agent across the blood-brain barrier comprising the artificial LDL particle of claim 1 and a pharmaceutically acceptable carrier.

20. A composition for delivery of an agent across the blood-brain barrier comprising the artificial LDL particle of claim 3 and a pharmaceutically acceptable carrier.

21. A composition for delivery of an agent across the blood-brain barrier comprising the artificial LDL particle of claim 4 and a pharmaceutically acceptable carrier.

22. The artificial LDL particle of claim 1, comprising a conjugate of cholesterol linked to the therapeutic agent, wherein the therapeutic agent is selected from the group consisting of: amino acids, peptides, proteins, nucleic acids, carbohydrates, drugs, and lipids.

23. The artificial LDL particle of claim 22, wherein the therapeutic agent is selected from the group consisting of: neurotrophic factors, growth factors, enzymes, antibodies, neurotransmitters, neuromodulators, antibiotics, antiviral agents, antifungal agents and chemotherapeutic agents.

24. The artificial LDL particle of claim 23, wherein the therapeutic agent is adriamycin.

25. A method of producing an artificial low-density lipoprotein (LDL) particle of claim 1 comprising the steps of: 1) suspending a mixture of phospholipids and lipids containing a therapeutic agent in a buffer solution; 2) sonicating the solution to form the outer phospholipid monolayer and solid lipid core; and 3) adding a solution comprising at least one cloned apolipoprotein, wherein the phospholipids and lipids are added in a ratio of between 11.5:1 and 12.5:1 by weight.

26. The method of claim 25, wherein the artificial LDL particle has a diameter between 10 and 50 nm.

27. The method of claim 25, wherein the therapeutic agent is conjugated.

28. The method of claim 27, wherein the therapeutic agent is conjugated to cholesterol.

29. The method of claim 28, wherein the therapeutic agent is conjugated to cholesterol through an ester bond.

30. An artificial low-density lipoprotein (LDL) particle comprising an outer phospholipid monolayer comprising egg yolk phosphatidyl choline and cloned ApoE3, and a solid lipid core comprising cholesterol oleate and a therapeutic agent.

31. The artificial LDL particle of claim 30, wherein the outer phospholipid monolayer further comprises one or more oxysterols and/or an additional apolipoprotein selected from the group consisting of ApoB and ApoE4.

32. The artificial LDL particle of claim 30, wherein the therapeutic agent is conjugated.

33. The artificial LDL particle of claim 32, wherein the therapeutic agent is conjugated to cholesterol.

34. The artificial LDL particle of claim 30, wherein the therapeutic agent is adriamycin.

35. The artificial LDL particle of claim 30, wherein the therapeutic agent is tetracycline.

36. An artificial low low-density lipoprotein (LDL) particle produced by a method comprising the steps of: 1) suspending a mixture of phospholipids and lipids containing a therapeutic agent in a buffer solution; 2) sonicating the solution to form the outer phospholipid monolayer and solid lipid core; and 3) adding a solution comprising at least one cloned apolipoprotein, wherein the phospholipids and lipids are added in a ratio of between 11.5:1 to 12.5:1 by weight, and wherein the at least one apolipoprotein is ApoE incorporated into the outer phospholipid monolayer.

* * * * *